(12) United States Patent
Wahl et al.

(10) Patent No.: US 6,359,960 B1
(45) Date of Patent: Mar. 19, 2002

(54) METHOD FOR IDENTIFYING AND LOCATING MARKERS IN A 3D VOLUME DATA SET

(75) Inventors: Eric Wahl, Erlangen; Uwe Weber; Norbert Rahn, both of Forchheim; Rainer Graumann, Hoechstadt, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/630,968

(22) Filed: Aug. 2, 2000

(30) Foreign Application Priority Data

Aug. 3, 1999 (DE) .......................... 199 36 364

(51) Int. Cl.[7] .............................................. A61B 6/03
(52) U.S. Cl. ............................................ 378/20; 378/4
(58) Field of Search ............................. 378/4, 8, 18, 20

(56) References Cited

U.S. PATENT DOCUMENTS

| 5,636,255 A | 6/1997 | Ellis ........................... 378/20 |
| 5,706,324 A | 1/1998 | Wiesent et al. ................ 378/4 |
| 6,206,566 B1 * | 3/2001 | Schuetz ....................... 378/205 |

FOREIGN PATENT DOCUMENTS

| DE | 41 20 676 C2 | 9/1994 |
| DE | 195 39 367 A1 | 4/1997 |

* cited by examiner

Primary Examiner—David V. Bruce
(74) Attorney, Agent, or Firm—Schiff Hardin & Waite

(57) ABSTRACT

In a method for automatically determining coordinates, relative to a reference coordinate system, of markers contained in a 3D volume data set of a subject provided with markers imaged in 2D projections of the 3D volume data set are detected, the centers of gravity of the imaged markers are determined, and back projection straight lines through the markers are established. The intersection points of the back projection straight lines with each other are identified, or the points with the smallest distance from one another on different back projection straight lines are determined if the back projection lines arc skewed. Spatially limited areas are identified, which contain an accumulation of intersection points of back projection straight lines or an accumulation of points with the smallest distance from one another. The coordinates of the centers of gravity of these spatially limited areas are calculated and are used as the coordinates for the respective markers.

8 Claims, 3 Drawing Sheets

METHOD FOR IDENTIFYING AND LOCATING MARKERS IN A 3D VOLUME DATA SET

BACKGROUND OF THE INVENTION

1. Field of the Invention

The present invention relates to a method for determining coordinates of markers contained in a 3D volume data set of a subject provided with markers, with respect to a reference system of coordinates.

2. Description of the Prior Art

In image processing, different procedures employing a 3D volume data set of a measuring subject are associated with the problem of reliably determining the three-dimensional coordinates of the markers contained in the 3D volume data set. Identification of such coordinates is needed in medical technology for example, in order to be able to navigate instruments relative to a patient or in order to be able to handle multi-modality image fusion, namely the superimposition of a number of images acquired by means of different image systems, with the markers as reference points.

U.S. Pat. No. 5,636,255 describes three different methods for determining the positions of markers contained in a data set of a subject provided with markers. In the first method the subject to be examined is disposed in a frame of known dimensions. The frame and the markers arranged at the subject are imaged in the CT data set that is obtained with respect to the subject. Due to the known dimensions of the frame, the positions of the markers imaged in the CT data set can be derived with respect to a reference system of coordinates. The second method for determining the positions of the markers is based on automatically estimating the centers of gravity of the markers in the CT data set, and the third method for determining the positions is based on the utilization of a mechanical pointer.

German OS 195 12 819 describes an X-ray computed tomography device with an X-ray source that emits an X-ray bundle that penetrates a measuring field, and with a detector. A 3D volume data set is to be generated by means of the X-ray computed tomography device; however, the knowledge of the exact pickup geometries with respect to each 2D projection, namely the exact knowledge of the position of the X-radiator and the detector, as well as their orientation relative to one another with respect to each 2D projection, is required. Since the X-ray computed tomography device has mechanical instabilities, markers are arranged in the measuring field, and these markers are imaged in the 2D projections and allow the determination of the pickup geometries for each 2D projection. This document, however, does not describe how the markers, particularly their coordinates, are detected.

German PS 41 20 676 describes a method for detecting small subjects in a natural environment using an electro-optical sensor that scans the surroundings and that is followed by an evaluation unit.

German OS 195 39 367 describes a method for transforming a system of coordinates.

The preferred method for determining the 3D coordinates of the markers in a 3D volume data set is an interactive identification and localization of the markers and therefore is characterized by interventions by a user (attendant, technician, physician, etc.); however, this is time-involved and error-sensitive.

SUMMARY OF THE INVENTION

An object of the present invention is to provide a method with which the coordinates of markers contained in a 3D volume data set can be automatically determined in a reliable way, without interventions by a user.

This object is achieved in accordance with the invention in a method for determining the coordinates of markers contained in a 3D volume data set of a subject, which is provided with markers, with respect to a reference system of coordinates, having the following method steps. A series of 2D projections are picked up by means of an X-ray system, which has an X-ray source and a planar X-ray detector, and the 3D volume data set is generated from the series of 2D projections. Alternatively a series of 2D central or 2D parallel projections are generated from an existing 3D volume data set of the subject. The markers imaged in the picked up or generated 2D projections are detected. For each detected marker, one reference point in the 2D projections is determined that represents the detected marker. Back projection straight lines are established that extend through the reference points such that, in the case of the 2D projections picked up by means of the X-ray system, each back projection straight line extends through the focus of the X-ray source. In the case of the generated 2D central projections, each back projection straight line proceeds through the projection point of the respective 2D central projection. In the case of the generated 2D parallel projections, each back projection straight line orthogonally intersects the planar 2D projection in the reference point, which 2D projection contains the imaged marker or the corresponding reference point. The intersection points of the back projection straight lines are identified or the points situated on different back projection straight lines are identified, which points have the smallest distance from one another given back projection straight lines that are skewed to one another. Spatially limited areas are formed which have an accumulation of intersection points or points having the smallest distance from one another. The coordinates of the center of gravity of each of the spatially limited areas are calculated.

The method makes it possible to fully automatically determine the coordinates of markers contained in a 3D volume data set in a desired way without interventions by a user. Even if, in a number of 2D projections that is comparatively low relative to the total number of the examined 2D projections, contents of the 2D projections are identified as markers in the marker detecting step, these erroneously identified "markers" are eliminated in the area formatting step, since the number of intersection points of the back projection straight lines and/or the spatial density of the points on the back projection straight line with the smallest distance from one another is too low in order to be combined in a spatially limited area. Conversely, should markers not be recognized as such in a number of 2D projections that is comparatively low relative to the total number of examined 2D projections, these undetected markers are still captured as a spatially limited area in the area forming step due to their recognition in other 2D projections in which the markers are imaged as well. This is because a sufficient number of intersection points of the back projection straight lines and/or of points lying on different back projection straight lines with smallest distance from one another occurs. These points being correspondingly close to one another. Therefore, the inventive method proceeds fully automatically not only when the coordinates of markers contained in a 3D volume data set are determined, but also works in a reliable manner, so that errors are practically excluded when the markers are identified and located.

In the present invention, a 3D volume data set is a data set of image data of a subject, from which different 3D images, which can represent different perspectives and sections of the subject, can be reconstructed.

In a version of the invention, the reference point, through which a back projection straight line extends, is the center of gravity of the marker. Using the center of gravity as the reference point has proven to be advantageous because it can be identified in a simple and defined manner for each detected marker. Therefore, it is not required to specifically specify how reference points are to be determined.

According to an embodiment of the invention, the detection of one or more markers that are imaged in a picked up or generated 2D projection is undertaken according to the following method steps. A 2D projection is divided into first surface elements. The picture element with the maximum or minimum light intensity is identified in each of these first surface elements. The local maximum and minimum of the light intensity in a second surface element of defined size is determined, which second surface element is positioned around the corresponding picture element, given an upward transgression or downward transgression of a first threshold value of the light intensity of such a picture element. A weighted difference is formed from the local maximum and minimum. The shape of a marker is developed when a second threshold value is exceeded by the weighted difference. Dependent on its shape, the marker is allocated to a marker type.

According to a version of the invention, when the shape of a marker is developed, the variance and/or the covariance and/or the correlation coefficients to adjacent picture elements in the plane of the 2D projection are determined in an iterative process—proceeding from the respective maximum or minimum- and/or the number of the picture elements are determined. The principal inertial axes of a marker candidate are calculated when the detected values of the variance and/or of the covariance and/or of the correlation coefficients and/or the number of the picture elements are situated in a fixed range of values. The position of the principal inertial axes of the marker candidate relative to one another in the plane of the respective 2D projection are compared to the position of the principal inertial axes of markers of a known type relative to one another. The edge lines for the potential markers are formed when the relative position of the principal inertial axes substantially coincide.

The markers, particularly the shapes of markers, are thus reliably detected or identified in the 2D projections, so that their centers of gravity can be detected without problems.

DESCRIPTION OF THE PREFERRED EMBODIMENTS

Figure 1:
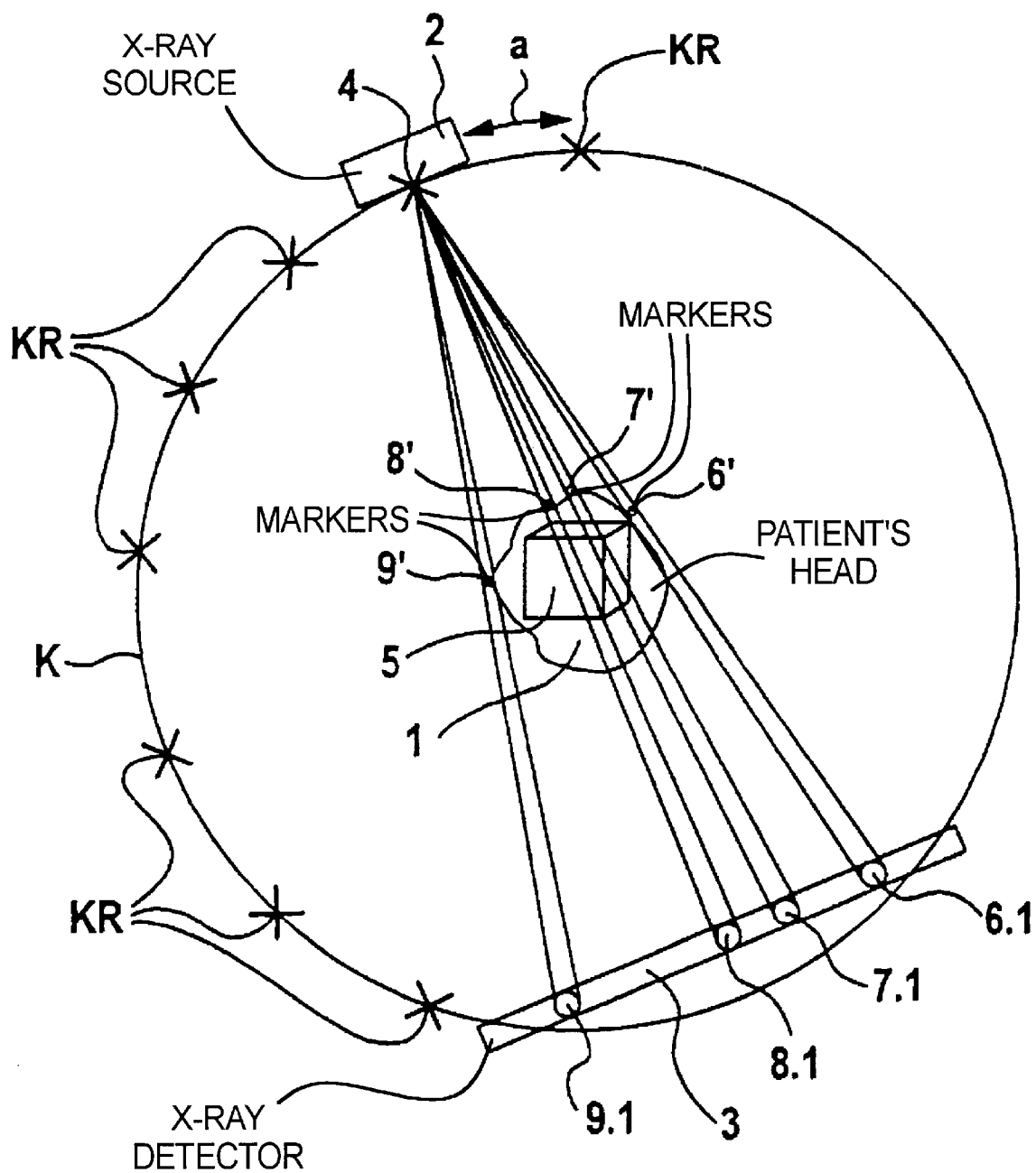
FIG. 1 schematically illustrates the pickup of central projections in the inventive method.

FIG. 1 schematically shows the pickup of central projections of a subject. In the exemplary embodiment, the subject is the head 1 of a patient (not shown in greater detail).

For picking up cental projections of the head 1 of the patient, an X-ray system, having an X-ray source 2 and a planar X-ray detector 3, is ideally moved on an orbit K around the head 1 of the patient, whereby 2D projections of the head 1 of the patient are sequentially picked up from different angles. For example, the X-ray system can be arranged (in a way that is not shown but that is known) at a C-arm of an X-ray device that is installed in mobile or stationary fashion. The C-arm can be displaced in a specific angle range along its circumference for picking up such 2D projections of the head 1 of the patient. FIG. 1 shows the adjustment movement of the X-ray system by means of the arrow a on the orbit K. The positions of the focus 4 of the X-ray source 2 for different 2D projections are indicated by means of crosses KR along the orbit K.

A 3D volume data set of the head 1 of the patient, by means of, for example, an image computer (not shown in FIG. 1), can be acquired from the series of 2D projections of the head 1 of the patient that are picked up upon rotation of the X-ray system. Different 3D images of the head 1 of the patient, which can show different perspectives and sections of the head 1, can be reconstructed from the data of this 3D volume data set. FIG. 1 shows a cuboid 5 as an example of such a reconstructable volume.

In the exemplary embodiment, X-ray-positive (radio-opaque) markers 6' through 9' are arranged at the head 1 of the patient, these markers 6' through 9' being imaged in the 2D projections of the head 1 and are therefore also contained in the 3D volume data set of the head 1 of the patient as markers 6 through 9. However, the markers 6 through 9 are not necessarily contained in each reconstructed 3D image of the head 1. For example, only the marker 6 is imaged in the reconstructable cuboid 5 shown in FIG. 1.

The markers 6 through 9 contained in the 3D volume data set and in the 3D images of the head 1 of the patient serve as reference points or fixed points in order to be able to navigate instruments relative to the head 1 during an operative intervention at the head 1 of the patient, or in order to be able to undertake a multi modality image fusion. For these applications, it is required to know the coordinates of the markers contained in the 3D images of the head 1 of the patient. The inventive automatic identification and localization for this purpose, for example with the aid of a computer (not shown), is as follows.

Figure 2:
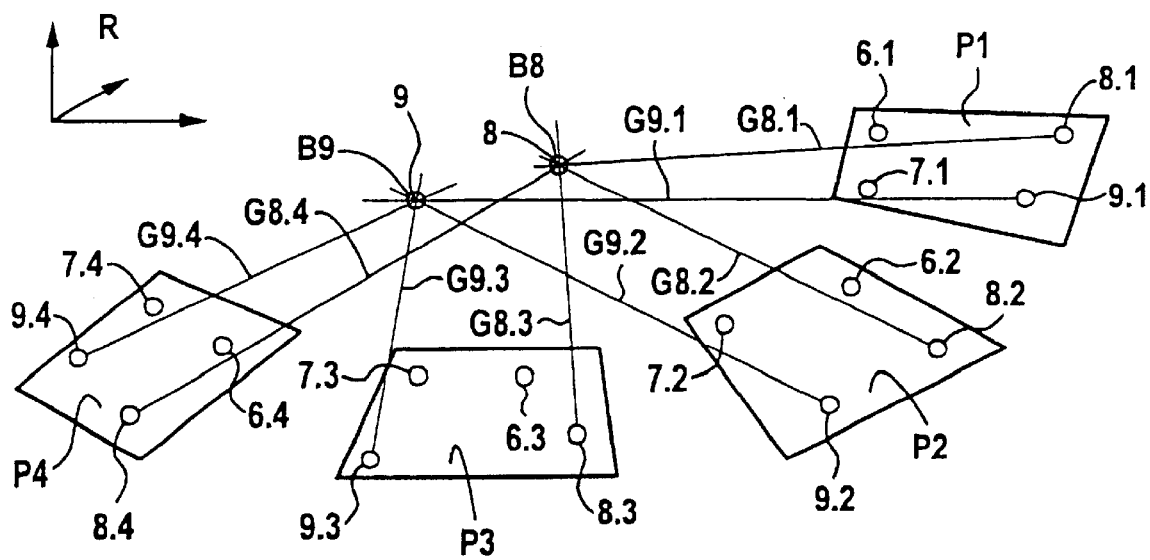
FIG. 2 illustrates the localization of markers in a 3D volume data set on the basis of acquired central projections in the inventive method.

For detecting the coordinates of the markers 6 through 9 contained in the 3D volume data set, use is made of the 2D projections, which have been detected and stored in the course of the measuring process and in which (at least) most of the markers are imaged. FIG. 2 shows four 2D projections P1 through P4 as an example, which have been picked up under different projection angles by means of the X-ray system and in which the markers are imaged.

Figure 3:
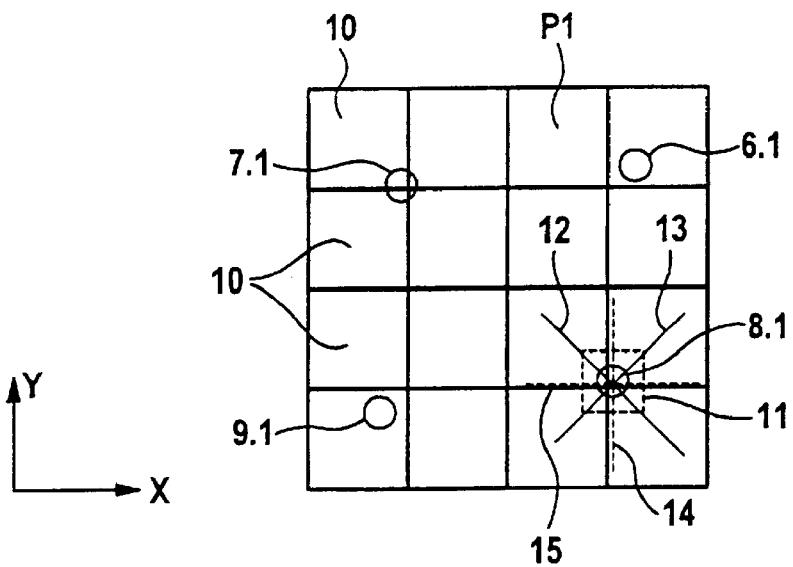
FIG. 3 illustrates the identification of markers in 2D projections in the inventive method.

Initially, the markers 6.1 through 9.4 imaged in the 2D projections P1 through P4 are detected. FIG. 3 illustrates, as an example, the detection of a marker at the 2D projection P1 on the basis of the marker 8.1 imaged in the 2D projection P1. The same method is used for the markers 6.1 through 9.4 imaged in the 2D projections PI through P4.

For this purpose, the projection P1 is completely divided into surface elements 10, preferably each of the same size. The picture element with the maximum or minimum light intensity is determined in each of the surface elements 10—the picture element with the maximum light intensity being determined in the exemplary embodiment due to the radiologically detected 2D projections. This is accomplished by investigating the surface elements 10 sequentially, for example. The maximum light intensity of a picture element detected in each surface element 10 is compared to a first threshold value that can be prescribed. In the exemplary embodiment, there is a changeover to the next surface element 10 when the threshold value is downwardly transgressed. However, when the detected light intensity lies above the threshold value, a second surface element 11 of defined size, which is fixed as a result of the maximum expansion of a marker, is positioned, preferably centrally around the picture element with the maximum light intensity of a surface element 10 (as this is shown in FIG. 3 for the imaged marker 8.1 to be detected, which is, until detection is concluded, a marker candidate). The local maximum and the local minimum of the light intensity are determined in the second surface element 11 and a weighted difference is formed from the local maximum and minimum. The maxima or minima in such second surface elements 11 are respectively determined in a system of coordinates for each 2D projection, with the position of the coordinate system being known vis-a-vis a reference coordinate system R of the volume data set. In the exemplary embodiment, the maximum and the minimum are provided in the plane of the projection P1 within a Cartesian x-y coordinate system. In the exemplary embodiment, the weighted difference is determined according to the equation $$K=n*(M-m)+m$$

wherein

M is the maximum m is the minimum, and n is an adaptively selectable weighting factor.

When the value of the weighted difference lies above a second threshold value, the second surface element 11 is a candidate for containing a marker, so that the examination is continued.

Proceeding from the local maximum, the variance and/or the covariance and/or the correlation coefficients, in an iterative process, are determined for the picture elements neighboring the maximum in the plane of the 2D projection, and the number of picture elements that exceed a fixable value of the light intensity are determined.

When the values of the variance and/or of the covariance and/or of the correlation coefficients and the number of the picture elements are situated in a range of values that is to be expected for an imaged marker, the presence of a marker is concluded and the principal inertial axes 12, 13 of the marker candidate 8.1 are calculated in the x-y-plane dependent on the determined values of the variance and/or covariance and/or correlation coefficients and the number of picture elements. Subsequently, the position of the determined principal inertial axes 12, 13 of the marker candidate 8.1 relative to one another is compared to the position of the principal inertial axes of markers of known type relative to one another. The inertial axes 12, 13 are rotated around their intersection point a specific angle, so that the position invariancies of the markers candidates are canceled. Such position invariancies with respect to the marker candidates occur as a result of the projections of the markers from different projection angles. The principal inertial axes 14, 15 of a known marker are shown as an example in FIG. 3; the positions of these principal inertial axes 14, 15 relative to one another corresponds substantially to the position of the principal inertial axes 12, 13 of the marker candidate 8.1 relative to one another.

Figure 4:
FIG. 4 illustrates the signature of a square marker in the inventive method.

When the position of the principal inertial axes of the marker candidate relative to one another substantially corresponds to the position of the principal inertial axes of a known marker relative to one another, the edge line for the detected, planarly imaged marker is formed on the basis of the signature of a detected marker. The signature is determined using known morphological operators. In order to be able to make conclusions about the signature, it is standardized with respect to its average value and its dynamics, i.e. the magnitudes of the amplitudes. When the imaged markers have edges, the number of maximum points in the signature characterizes the number of edge points of a marker. FIG. 4, as an example, shows the signature for a square marker, whereby four maximum points characterize the four edges of the square marker.

Finally, the signature of a marker candidate is compared to the ideal signatures of known markers with respect to the standard deviation and the number of edge points. When the signature of the marker candidate corresponds, for example, sufficiently enough to an ideal signature of a known marker, the marker candidate is type-categorized as such and the edge line of the marker is formed. In the exemplary embodiment, the marker 8 that belongs to the imaged marker 8.1 is typed as a spherical marker.

The types of the other markers imaged in the 2D projection P1, or in the other 2D projections, are determined in the same way as for the marker 8 or, more specifically, for its image 8.1 in the 2D projection P1.

Subsequent to the detection or typing of the markers 6.1 through 9.4 imaged in the 2D projections, a reference point, preferably the center of gravity of the detected marker in the plane of the respective 2D projection, is determined for each detected marker.

As shown as an example in FIG. 2 on the basis of the projections P1 through P4 for the imaged markers 8.1 through 8.4 and 9.1 through 9.4, back projection straight lines G8.1 through G8.4 and G9.1 through G9.4, which respectively extend through the centers of gravity of markers 8.1 through 8.4 and 9.1 through 9.4 imaged in the 2D projections P1 through P4, as well as through the focus 4 of the X-ray source 2, are established. These back projection straight lines G8.1 through G8.4 and G9.1 through G9.4 project the centers of gravity of the markers 8.1 through 8.4 and 9.1 through 9.4 imaged in the 2D projections back into the 3D volume.

For locating all markers 6 through 9 in the 3D volume, the intersection points of all back projection straight lines with one another are determined. When back projection straight lines are skewed to one another, the points lying on different back projection straight lines are determined, which points have the smallest distance from one another. Spatially limited areas, which are referred to as clusters are formed from a spatial accumulation of such intersection points, or of such points with the smallest distance from one another, and their centers of gravity are determined. The centers of gravity of the clusters, or their coordinates with respect to the reference coordinate system R, finally form the coordinates of the markers 6 through 9 in the 3D volume data set, which markers 6 through 9 are to be detected.

In the exemplary embodiment, the straight lines G8.1 through G8.4 ideally intersect in a single intersection point, namely in the center of gravity of the marker 8. In the same way, FIG. 2 illustrates the detection of the center of gravity for the marker 9, whereby the straight lines G9.1 through G9.4 ideally intersect in the center of gravity of the marker 9. In the general case, an inordinate accumulation of intersection points of the back projection straight lines G8.1 through G8.4, or G9.1 through G9.4 occurs, or an accumulation of points with smallest distance from one another in the 3D volume occurs, when the back projection straight lines are skewed to one another. The actual positions of the markers 8 and 9 in the 3D volume are determined by means of pattern recognition, whereby the markers 8 and 9 are characterized by clusters B8 or B9, which respectively include a condensed "point cloud" (bi-variate point distribution) of the intersection points of the back projection straight lines, or of the points of the back projection straight lines with smallest distance from one another, in the 3D volume.

The centers of gravity of the clusters B8 and B9 finally form (as it has already been mentioned) the coordinates of the markers 8 and 9 in the 3D volume data set.

The detection of markers in a 3D volume data set has been described on the basis of FIG. 2, whereby the 3D volume data set has been generated from 2D projections picked up by means of an X-ray system that can be adjusted on an orbit.

The inventive method also can be applied with respect to an already existing 3D volume data sets containing markers that have been acquired by means of MR, CT or nuclear medicine devices.

Given an already generated 3D volume data set, 2D projections must be initially generated from the 3D volume data set by means of methods that are known, such as maximum intensity projection (MIP), for implementing the inventive method.

When central projections are generated from the 3D volume data set, the further steps of the method for determining the coordinates of markers contained in the 3D volume data set corresponds to the steps described in connection with FIG. 2, but the back projection straight lines do not extend through the center of gravity of the detected markers and the focus, but through the center of gravity of the detected markers and the projection point of the central projections that corresponds to the focus.

Figure 5:
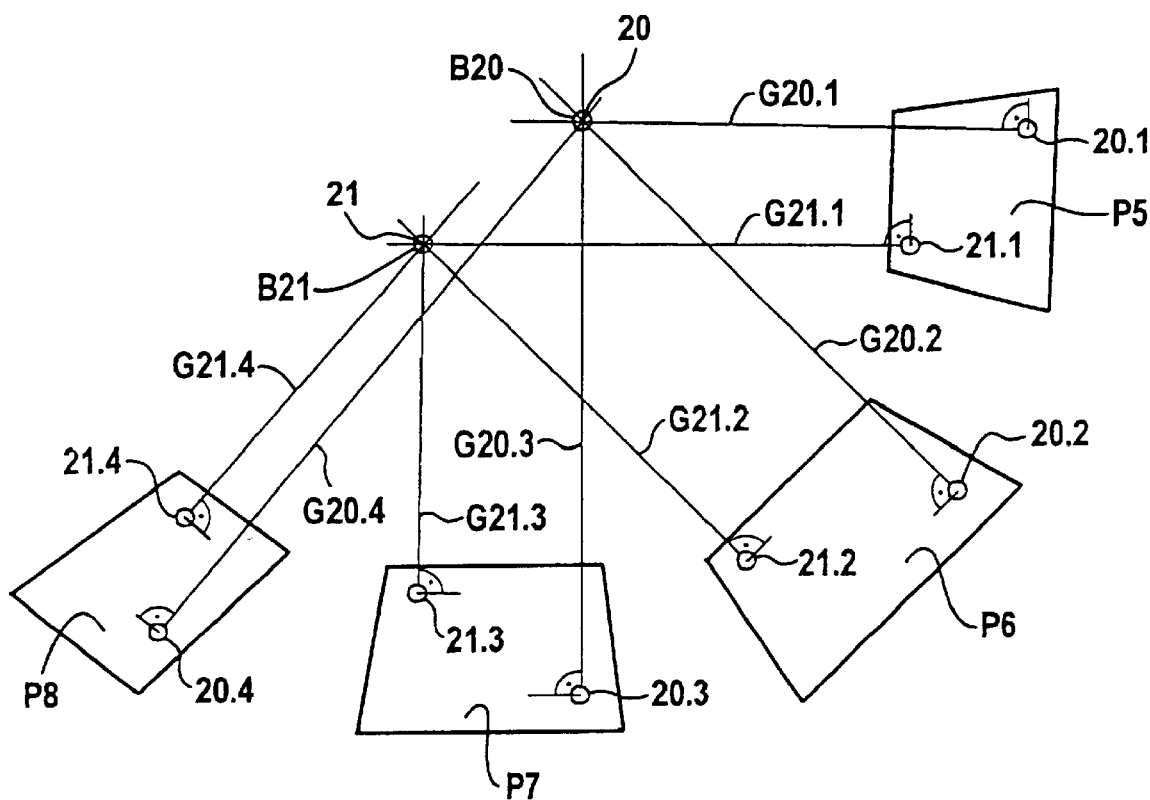
FIG. 5 illustrates the localization of markers in a 3D volume data set on the basis of parallel projections in the inventive method.

Given the generation of parallel projections from a 3D volume data set (as shown in FIG. 5), the steps of the method for determining the coordinates of the markers contained in the 3D volume data set essentially correspond to the method described in connection with FIG. 2. The only difference is with respect to the setup of the back projection straight lines. In the case of the parallel projections generated from a 3D volume data set, these extend through the centers of gravity of the markers imaged and detected in the 2D projections, orthogonally and intersect the planes of the 2D projections containing the centers of gravity.

FIG. 5 shows an example of the determination of the coordinates of the centers of gravity for two markers 20, 21 contained in a 3D volume data set, which markers 20, 21 are imaged in parallel projections P5 through P8. Subsequent to the detection of the markers in the parallel projections P5 through P8 and subsequent to the determination of the centers of gravity of the markers 20.1 through 21.4 imaged in the parallel projections (as described in connection with FIG. 2), the back projection straight lines are established such that each back projection straight line G20.1 through G20.4, or G21.1 through G21.4, extends through the marker 20.1 through 20.4, or 21.1 through 21.4, allocated to it and orthogonally intersects the planes of the 2D projection P5 through P8, which contain the marker or the center of gravity of the marker. Ideally, the intersection point of the back projection straight line G20.1 through G20.4 is situated in the center of gravity of the marker 20 and the intersection point of the back projection straight line G21.1 through G21.4 is situated in the center of gravity of the marker 21. The coordinates of the centers of gravity of the markers 20, 21 defined in this way can be determined in a known way.

In the most general case, the intersection points of the back projection straight lines or, when the back projection straight lines are skewed to one another, the points of the back projection straight lines with the smallest distance from one another, will form condensed point clouds, which are included in clusters B20 and B21, whose centers of gravity characterize the positions of the markers 20 and 21 given parallel projections generated from a 3D volume data set as well.

The inventive method has been explained above by using medical imaging as an example, however, the inventive method is not limited to medical applications.

When the markers in the 2D projections are characterized by areas with the lowest light intensity, their detection in the 2D projections—in contrast to the previously described exemplary embodiment—ensues by means searching in a planar element of the 2D projection for the picture element with the minimum light intensity. In this case, the examination of the environment of the picture element for identifying a marker is always continued when a first threshold value is downwardly transgressed. The further steps are analogous to the previously described steps.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining respective coordinates of markers, relative to a reference coordinate system, in a 3D data set representing a subject on whom said markers are disposed, said method comprising the steps of:

(a) picking up a series of 2D projections of a subject on whom a plurality of x-ray detectable markers are disposed, using an x-ray source having a focus from which an x-ray beam is emitted and an x-ray detector on which said x-ray beam is incident, with said subject being disposed in said x-ray beam, said 2D projections, in combination, forming a 3D data set of said subject;

(b) identifying said markers in each of said 2D projections;

(c) in each of said 2D projections, determining respective reference points representing images of said markers in that 2D projection;

(d) for each of said reference points in each of said 2D projections, identifying back projections straight lines proceeding through the reference point and through the focus of the x-ray source;

(e) for any of said back projections straight lines that intersect, identifying an intersection point, and for any of said back projection straight lines that do not intersect, identifying respective points on said back projection straight lines that have a smallest distance from one another;

(f) identifying respective spatially limited areas containing an accumulation of said intersection points and said points having a smallest distance from one another; and (g) calculating respective coordinates in said reference coordinate system of respective centers of gravity of said areas, and using said coordinates of said centers of gravity as respective coordinates in said reference coordinate system for said markers.

2. A method as claimed in claim 1 wherein step (c) comprises defining the respective reference points in said 2D projections as the respective centers of gravities of the images of said markers in the respective 2D projections.

3. A method as claimed in claim 1 wherein said plurality of markers includes markers of respectively different marker types, and comprising the additional steps of:

dividing each of said 2D projections into a plurality of first surface elements;

in each of said first surface elements in each of said 2D projections, determining picture elements having an extreme light intensity, selected from the group consisting of maximum light intensity and minimum light intensity;

for each of said picture elements having an extreme light intensity, defining a second surface element of a predetermined size around the picture element having an extreme light intensity and, within said second surface element, identifying a local maximum light intensity given an upward transgression of a first threshold value for light intensity and identifying a local minimum light intensity given a downward transgression of said first threshold;

for each second surface element, forming a weighted difference from said local maximum light intensity and said local minimum light intensity;

determining a shape of said marker dependent on a relationship of said weighted difference to a second threshold value; and allocating a marker type to said marker dependent on said shape.

4. A method as claimed in claim 3 wherein the step of determining the shape of said marker comprises:

in an iterative process, proceeding from said local maximum, for picture elements in said second surface element determining whether a characteristic of each of said picture elements within said second surface element is within a predetermined range, said at least one characteristic being selected from the group consisting of variance, co-variance, correlation coefficient, and number of picture elements;

for said picture elements, as a group, in said second surface element having said at least one characteristic in said range, determining principal inertial axes for said group of picture elements, said principal inertial axes being in a coordinate system for the respective 2D projection containing said second surface element;

comparing a position of said principal inertial axes of said group of picture elements to a position of a principal inertial axes of markers of respectively different marker types and identifying said picture element group as representing a marker of the marker type having principal inertial axes most closely corresponding to said principal inertial axes of said group of picture elements; and from the principal inertial axes of said group of picture elements and from said identification of marker type, identifying edge lines for a marker represented by said group of picture elements.

5. A method for determining respective coordinates of markers, relative to a reference coordinate system, in a 3D data set representing a subject on whom said markers are disposed, said method comprising the steps of:

(a) from an existing 3D data set of a subject on whom a plurality of x-ray detectable markers were disposed, generating a plurality of 2D projections selected from the group consisting of 2D central projections and 2D parallel projections;

(b) identifying said markers in each of said 2D projections;

(c) in each of said 2D projections, determining respective reference points representing images of said markers in that 2D projection;

(d) for each of said reference points in each of said 2D projections, identifying back projections straight lines proceeding through the reference point and orthogonally intersecting a plane containing the 2D projection;

(e) for any of said back projections straight lines that intersect, identifying an intersection point, and for any of said back projection straight lines that do not intersect, identifying respective points on said back projection straight lines that have a smallest distance from one another;

(f) identifying respective spatially limited areas containing an accumulation of said intersection points and said points having a smallest distance from one another; and (g) calculating respective coordinates in said reference coordinate system of respective centers of gravity of said areas, and using said coordinates of said centers of gravity as respective coordinates in said reference coordinate system for said markers.

6. A method as claimed in claim 5 wherein step (c) comprises defining the respective reference points in said 2D projections as the respective centers of gravities of the images of said markers in the respective 2D projections.

7. A method as claimed in claim 5 wherein said plurality of markers includes markers of respectively different marker types, and comprising the additional steps of:

dividing each of said 2D projections into a plurality of first surface elements;

in each of said first surface elements in each of said 2D projections, determining picture elements having an extreme light intensity, selected from the group consisting of maximum light intensity and minimum light intensity;

for each of said picture elements having an extreme light intensity, defining a second surface element of a predetermined size around the picture element having an extreme light intensity and, within said second surface element, identifying a local maximum light intensity given an upward transgression of a first threshold value for light intensity and identifying a local minimum light intensity given a downward transgression of said first threshold;

for each second surface element, forming a weighted difference from said local maximum light intensity and said local minimum light intensity;

determining a shape of said marker dependent on a relationship of said weighted difference to a second threshold value; and allocating a marker type to said marker dependent on said shape.

8. A method as claimed in claim 7 wherein the step of determining the shape of said marker comprises:

in an iterative process, proceeding from said local maximum, for picture elements in said second surface element determining whether a characteristic of each of said picture elements within said second surface element is within a predetermined range, said at least one characteristic being selected from the group consisting of variance, co-variance, correlation coefficient, and number of picture elements;

for said picture elements, as a group, in said second surface element having said at least one characteristic in said range, determining principal inertial axes for said group of picture elements, said principal inertial axes being in a coordinate system for the respective 2D projection containing said second surface element;

comparing a position of said principal inertial axes of said group of picture elements to a position of a principal inertial axes of markers of respectively different marker types and identifying said picture element group as representing a marker of the marker type having principal inertial axes most closely corresponding to said principal inertial axes of said group of picture elements; and from the principal inertial axes of said group of picture elements and from said identification of marker type, identifying edge lines for a marker represented by said group of picture elements.

* * * * *